United States Patent [19]

Donohue

[11] 4,154,922

[45] May 15, 1979

[54] POLYESTERS OF METHYL-SUBSTITUTED POLYPHENYLCARBOXYLIC ACIDS

[75] Inventor: John A. Donohue, Elmhurst, Ill.

[73] Assignee: Standard Oil Company (Indiana), Chicago, Ill.

[21] Appl. No.: 622,656

[22] Filed: Oct. 15, 1975

Related U.S. Application Data

[63] Continuation-in-part of Ser. No. 517,506, Oct. 24, 1974, abandoned.

[51] Int. Cl.$^2$ .................... C08G 63/18; C08G 69/26; C08G 69/32; C08G 69/40

[52] U.S. Cl. ........................ 528/308; 528/84; 528/183; 528/190; 528/295; 528/298; 528/337; 528/344; 528/347; 528/348; 560/76; 560/101; 562/488; 562/492

[58] Field of Search ........... 260/47 CZ, 47 CP, 78 R, 260/75 R, 515 P; 528/308, 84, 183, 190, 295, 298, 337, 344, 347, 348

[56] References Cited

FOREIGN PATENT DOCUMENTS 48-43670  12/1973  Japan .................................... 260/515 P

OTHER PUBLICATIONS

Nomura et al., J. Chem. Soc., (B), pp. 956–960.
Wagner et al., Synthetic Organic Chem., John Wiley & Sons, Inc., N.Y., N.Y., pp. 412–415, (1965).

*Primary Examiner*—Lester L. Lee
*Attorney, Agent, or Firm*—William C. Clarke; Arthur G. Gilkes; William T. McClain

[57] ABSTRACT

Methyl-substituted polyphenylacyl compounds are prepared by selective oxidation of oligomers of mesitylene. These methyl-substituted polyphenylacyl compounds are useful as intermediates for polyamides and polyesters. The esters are useful as plasticizers for polyvinylchloride.

8 Claims, No Drawings

POLYESTERS OF METHYL-SUBSTITUTED POLYPHENYLCARBOXYLIC ACIDS

BACKGROUND OF THE INVENTION

This application is a continuation-in-part of application Ser. No. 517,506 filed Oct. 24, 1974 now abandoned.

The field of this invention relates to aromatic polyacyl compounds of polyphenyl structure suitable for polymers useful for forming shaped objects, such as film, fiber and molded parts. The esters are suitable as plasticizers for polyvinylchloride and other polymers.

As is well known, the mechanical and physical properties of a fiber or film depend on the chemical structure of the polymer from which they are made. For example, the melting point, molding temperature, and glass transition temperature of the polymer composition control many of the physical properties and fabrication of the shaped objects. The melting point determines thermal resistance and heat-setting temperature of fibers. Molding temperature determines fabrication temperature. Glass transition temperature (Tg) determines initial modulus, tensile strain recovery, work of recovery, drape and hand, wash-and-wear characteristics, comfort factors and resilience of fibers. The main molecular factors which influence these properties include chain stiffness, the intermolecular forces, orientation and crystallinity.

Accordingly, there has been considerable interest in developing aromatic symmetrical acids as precursors for thermally stable polymers, such as polyesters or polyamides. It is well known that the introduction of aromatic units in the polymer chain backbone results in high bond energies, a low degree of reactivity, and rigidity of the polymer chain structure. The use of aliphatic units in the polymer chain backbone results in flexibility, lower temperature characteristics and decreased strength as compared with the aromatic types.

Substantially all commercial polyester fibers are based on terephthalic acid. While these fibers have many excellent properties there is a need for polyester fibers having a higher Tg than provided by terephthalic acid polyesters. Recently, 2,6-naphthalene dicarboxylic acid has been proposed as a suitable aromatic acid for producing polyesters suitable for tire cord. This acid provides polyesters having a higher Tg than those based on terephthalic acid. For example, poly(ethylene terephthalate) has a Tg of 74° C. while poly(ethylene 2,6-naphthalate) has a Tg of 115°–125° C. However, the difficulties of manufacturing the precursor, i.e., 2,6-dimethylnaphthalene, have made the production of this acid technically difficult and economically costly. The acid can require a four-step synthesis with attendant loss in yield and consequent high cost.

Various other organic polymers have been suggested for use as high temperature fibers, such as copolyamides (Kevlar), polybenzimidazoles, polyoxadiazoles, polyimides and phenylene ring systems (polyphenylenes). Polyarylates and polycarbonates have been suggested for use as engineering plastics. However, all of these are costly and/or difficult to manufacture. Accordingly, there is a need for new aromatic acids suitable for preparing polymers for many uses.

It is the object of this invention to provide a new group of aromatic polycarboxylic acids of polyphenyl structure which will meet this need. Another object of this invention is to provide a process for making these acids. Another object of this invention is to provide a new polycarboxylic acid, specifically 2,2',6,6'-tetramethylbiphenyl-4,4'-dicarboxylic acid, for use in polymer chains. A further object is to provide novel polymers, both polyamides and polyesters, made from these acids. Other and further objects of this invention will be apparent from the following description.

The field of this invention, accordingly, has three aspects. First it relates to novel compositions of matter which are methyl-substituted polyphenylacyl compounds and to the method of preparing these acyl compounds. Second, it relates to novel polyamides based on methyl-substituted polyphenylacyl compounds. Third, it relates to novel polyesters based on these same novel acyl compounds.

These novel methyl-substituted polyphenylacyl compounds (acids, acyl halides, simple esters, e.g., methyl, etc.) are desirable intermediates for producing condensation polymers, such as polyamides and polyesters suitable for shaped articles such as film, fiber and molded parts. The esters of these acids and monohydric alcohols containing 4 to 24 carbon atoms can be used as plasticizers for polyvinylchloride (PVC).

The abstract of an article by Y. Nomura and Y. Takeuchi (J. Chem. Soc. (B) 1970, 956–960) mentions the structure 2,2',6,6'-tetramethylbiphenyl-4,4'-dicarboxylic acid and its methyl ester but no further references to the compounds or to their properties or preparation are given in the abstract or in the article. There is no indication that these compounds were made nor suggestion how to make these compounds. Low yields of other substituted biphenyls are reported by the authors. For example, 4.8 grams of 4,4'-diamino-2,2',6,6'-tetramethylbiphenyl were prepared in 52% yield from 3,5-dimethylnitrobenzene which in turn yielded only 0.10 grams of 4,4'-dicyano-2,2',6,6'-tetramethylbiphenyl in 2% yield, and an overall yield of only 1% to the dicyano compound.

It has been found, in accordance with this invention, that the para carboxylic acid polyphenyls may be prepared in a very convenient manner by the oxidation of the para methyl groups of the methyl-substituted polyphenyls, e.g., bimesityl, by means of molecular oxygen in the presence of a cobalt compound, as for example; cobaltic acetate, and the process is especially convenient and advantageous if carried out in the presence of acetic acid. Ortho-methyl groups, the 2 and 6 methyl substituents of the polyphenyls, were found to require more severe oxidizing conditions; thus the pentacarboxylic biphenyl was found to require more severe oxidative conditions with the utilization of molecular oxygen in the presence of cobalt and manganese acetate, acetic acid, sodium bromide, and tetrabromomethane.

It has been found also that the novel polyesters prepared from the methyl-substituted diphenylcarboxylic acids and dihydric alcohols, such as those having two to ten carbon atoms unexpectedly possess high second order transition temperatures (Tg), transparency, colorlessness and toughness. These novel polyesters can be made into tough films and fibers. Molding temperature of the ethylene glycol polyester is unexpectedly low, with resultant savings in fabrication heat input. Density of the ethylene glycol polyester is 15 to 20% less than the density of poly(ethylene terephthalate), with resultant weight advantage over PET. The limiting oxygen index (LOI) of the ethylene glycol polyester of this invention is approximately 5% more than that of PET with resultant improved non-burning characteristics.

In recent years a limited amount of work has been done involving p,p'-bibenzoic acid and its esters in connection with homopolyesters. U.S. Pat. No. 3,008,929, for example, indicates that this work was not generally fruitful, for a homopolyester of bibenzoic acid and a glycol (e.g., polyethylenebibenzoate) possesses an extremely high melting point making its use in shaped articles entirely impractical, particularly when attempts are made to use it as a film or fiber-forming material. Also, known polybibenzoates exhibit an extremely high rate of crystallization, making orientation of fibers or films therefrom extremely difficult and costly, if not impossible, from a commercial viewpoint. The novel homopolymer polyesters prepared from the methyl-substituted polyphenylcarboxylic acids of this invention, quite unexpectedly in view of the experiences described above, make tough films and fibers with very desirable properties.

SUMMARY OF THE INVENTION

The novel compositions of matter are methyl-substituted polyphenyl acyl compounds of the formula

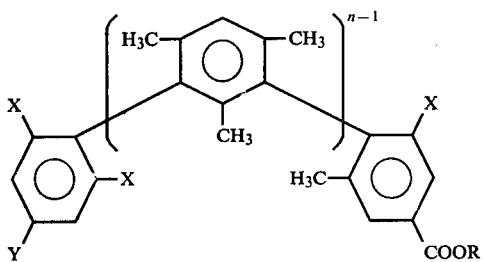

wherein n is a whole number from 1 to 3 inclusive, Y is selected from the class consisting of methyl and —COOR, and each R is hydrogen or a monovalent organic group of 1 to 24 carbon atoms, preferably methyl, when Y is methyl each X is methyl, and when Y is —COOR each X is independently selected from the class consisting of methyl and —COOR.

The monohydric alcohol esters of the methyl-substituted carboxylic acids are plasticizers for polyvinylchloride. The diacyl compounds can be reacted with compounds capable of forming amides to form novel polyamides for film and fiber applications. The diacyl compounds when reacted with dihydric alcohols, such as those having two to ten carbon atoms, form novel polyesters for film and fiber applications.

DETAILED DESCRIPTION OF THE INVENTION

In general, the novel methyl-substituted polyphenylacyl compounds of this invention are produced by the oxidation of at least one paramethyl group of a polymesityl compound.

The novel compositions of matter are methyl-substituted polyphenylacyl compounds of the formula

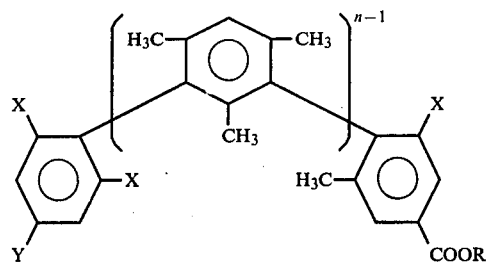

wherein n is a whole number from 1 to 3 inclusive, Y is selected from the class consisting of methyl and —COOR and R is hydrogen or a monovalent organic group of 1 to 24 carbon atoms, preferably methyl, when Y is methyl, each X is methyl and when Y is —COOR, each X is independently selected from the class consisting of methyl and —COOR. Among the specific acids which are embodiments of these novel compositions of matter are 2,2',4,6,6'-pentamethylbiphenyl-4'-carboxylic acid; 2,2',-6,6'-tetramethylbiphenyl-4,4'-dicarboxylic acid; 2-methylbiphenyl-2',4,4',6,6'-pentacarboxylic acid; 2,2',2'',4,4',6,6',6''-octamethyl-m-terphenyl-4''-carboxylic acid; 2,2',2'',4',6,6',6''-heptamethyl-m-terphenyl-4,4''-dicarboxylic acid; 2,2',2'',2''',4,4',4'',6,6',6'',6'''-undecamethyl-m-quaterphenyl-4'''-carboxylic acid; 2,2',2'',2''',4',4'',6,6',6'',-6'''-decamethyl-m-quaterphenyl-4,4'''-dicarboxylic acid; 2,2',2'',2''',2'''',4,4',4'',4''',6,6',6'',6''',6'''' - tetradecamethyl-m-quinquephenyl-4''''-carboxylic acid; 2,2',2'',2''',2'''',4',4'',4''',6,6',6'',6''',6''''-tridecamethyl-m-quinquephenyl-4,4''''-dicarboxylic acid and the methyl esters of these acids.

While the polymesitylenes useful in this invention can be produced by any technique, I have found that anodic electrochemical coupling of polymethylsubstituted benzenes is particularly useful. The electrolytic coupling of polymethylbenzene to its biphenyl derivatives has been reported by L. Eberson and K. Nyberg ("Anodic Oxidations", ACS Div. of Pet. Chem., Chicago, Vol. 15, No. 4, Sept. 1970, B7).

The required electrolytic reactions were carried out by applying a source of direct current to two electrodes in an electrically conducting solution of the organic compounds. Since most organic compounds are non-conductors, acids, bases, or salts were necessary to provide electrical conductivity. These substances must be chosen so that their reduction or oxidation occurs with more difficulty than that of the organic compound. For anodic processes in non-aqueous solvents it is well-known that tetrafluoroborates, fluorophosphates, nitrates, among others can be used as electrolytes. It is also known that solvents which have sufficiently high dielectric constants to promote ionization of the electrolyte when used alone are acetonitrile, dimethylformamide, propylene carbonate and methylene chloride. Electrolytes used with these solvents can be tetraalkylammonium salts or lithium salts. Since the voltage necessary to carry out the electrolysis depends upon the resistance of the solution for non-aqueous solutions, a voltage of 100 volts can be necessary under laboratory conditions to obtain a current flow with a reasonable magnitude where resistances of 1000 ohms or higher are present.

The yield of any oligomer can be maximized by carefully selecting process conditions. The electrolyte composition, cell design and temperature variations must be controlled to permit removal of the desired oligomer from solution before its concentration becomes too large. This prevents its conversion to higher oligomers if it remains dissolved or its precipitation on the anode. Lower oligomers can be separated and recycled to extinction.

Good yields of bimesityl and other oligomers are possible if the oligomers are removed rapidly enough. The product of the anodic coupling is a heavy solute which progressively separates out of the electrolyte. The product can be recovered by cooling the solute and electrolyte mix to −20° C. when moderate quantities have been converted. A preferable method of recovery is by solvent extraction when low to moderate quantities have been converted. Aliphatic hydrocarbons of a lower boiling point than that of the product are utilized as the extracting medium. Heptane was utilized in this instance.

A divided cell is often used in electrolyses. The cathode is separated from the anode by means of a diaphragm, often porous alumina, to prevent the reduced product from being re-oxidized. In this instance, a polyethylene screen was used to electrically insulate the cathode from the anode and not as a diaphragm. The optimum current density varies but it is generally between 0.02 and 0.2 amp/sq. cm. The actual number of ampere-hours is normally substantially greater than the theoretical (53.6 ampere hours per mole of product, assuming two electrons per molecule of reagent) and was approximately two-times greater in the case of bimesityl.

Separation of the bimesityl and other oligomers was by fractional distillation followed by a purifying distillation. The batch fractional distillation to obtain the crude oligomers was performed by well-known methods. Since these materials are high melting point solids, the entire purifying distillation was conducted within an oven at a temperature above the melting point but below the boiling point of the compound.

Suitable polymesitylenes useful for producing the acids of this invention include 2,2',4,4',6,6'-hexamethylbiphenyl; 2,2',2",4,4',4",6,6',-6"-nonamethyl-m-terphenyl; 2,2',2",2'",4,4',4",4'",6,6',6",6'"-dodecamethyl-m-quaterphenyl which are, respectively, the bimesityl, the termesityl and the quatermesityl. Similarly, 2,2',2",2'",2"",4,4',4",4'",4"",-6,6',6",6'",6""-pentadecamethyl-m-quinquephenyl, which is the quinquemesityl, the hexamesityl and the higher oligomers of mesitylene are useful for producing the acids of this invention.

Irrespective of how the polymesitylenes are produced, at least one of the paramethyl (4 or 4') groups on a mesityl ring having only one direct bond to another mesityl ring is oxidized with molecular oxygen (e.g. $O_2$ gas or air) to the carboxylic acid function in liquid phase processes preferably employing acetic acid as reaction solvent.

I have found, in accordance with my invention, that new polyphenylcarboxylic acids containing no more than one acyl moiety on any aromatic ring of the polyphenyl carboxylic acid can be prepared in a very convenient method by mild oxidation of the polymesitylene using a cobalt catalyst. While the reaction can be carried out neat, it is generally preferred to use an organic solvent, preferably an organic acid, to prevent sublimination of the polymesityl. In the process only the methyl groups para to a biphenyl linkage are oxidized.

In this process, the polymesityl compound can be reacted with an oxygen-containing gas (oxygen, air, etc.) in the presence of cobaltic ions at a temperature within the range of 20° to 150° C., desirably 70° to 120° C., preferably 90° to 115° C., and at a pressure which maintains the organic acid (e.g. acetic acid) in the liquid phase. This general type of mild oxidation is described by T. Morimoto and Y. Ogata, (J. Chem. Soc. (B) 62, 1353 (1967)), which is incorporated by reference and employs oxygen and cobaltic acetate in acetic acid solution at 90° C. Suitable organic carboxylic acids which can be used as a solvent include acetic acid, propionic acid, etc. Approximately 0.01 to 3 parts by weight cobaltic ion per part by weight polymesityl compound can be used. In general, the higher the concentration of cobaltic ion the faster the rate of oxidation. The concentration of oxygen is not critical but should be in excess of theoretical. The time of the reaction is generally a function of the temperature and pressure. The higher the temperature, the faster the reaction. The acid can be isolated by conventional means or esterified with a lower alcohol (methanol, ethanol, isoproanol, to facilitate separation and purification.

Among the specific acids which are prepared by this technique are 2,2',4,6,6'-pentamethylbiphenyl-4'-carboxylic acid; 2,2',6,6'-tetramethylbiphenyl-4,4'-dicarboxylic acid; 2,2',2",4,4',6,6',6"-octamethyl-m-terphenyl-4"-carboxylic acid; 2,2',2",4',6,6',6"-heptamethyl-m-terphenyl-4,4"-dicarboxylic acid; 2,2',2",2'",4,4',4",6,6',6",6'"-undecamethyl-m-quaterphenyl-4'"-carboxylic acid; 2,2',2",2'",4',4",6,6',-6",6'"-decamethyl-m-quaterphenyl-4,4'"-dicarboxylic acid; 2,2',2",-2'",2"",4,4',4",4'",6,6',6",6'",6""-tetradecamethyl-m-qinquephenyl-4""-carboxylic acid; 2,2',2",2'",2"",4',4",4'",6,6',6",6'",6""-tridecamethyl-m-quinquephenyl-4,4""-dicarboxylic acid.

In the case where it is desired to produce polyphenyl compounds having more than one acyl group per aromatic ring, other techniques can be employed such as a liquid phase oxidation process using molecular oxygen catalyzed by the conjoint presence of a metal and bromine, as is taught in U.S. Pat. No. 2,833,816 which is incorporated by reference. This technique employs an acid medium, preferably acetic acid medium, and a heavy metal catalyst, preferably consisting essentially of cobalt and/or manganese, with a source of bromine ion to enhance the catalytic effect of the metal ion. The polymesityl compound can be reacted with an oxygen-containing gas (oxygen, air, etc.) at a temperature within the range of 120° to 275° C., desirably 150° to 250° C., and preferably 170° to 225° C., and at a pressure which maintains the organic acid (acetic acid, propionic acid, etc.) in the liquid phase at such temperature range. The ratio of total oxygen fed into the reaction mixture relative to the hydrocarbon can be in the range of about 2 to 500 moles of oxygen per mole of substituted hydrocarbon, desirably in the range of 5 to 300, and preferably in the range of 5 to 75. Generally the pressure can be in the range of atmospheric up to about 1500 p.s.i.g. Among the specific acids which can be prepared by this method is 2-methyl-2,2',4,4',6,6'-pentacarboxylic acid.

2,2',6,6'-Tetramethylbiphenyl-4,4'-dicarboxylates and the esters of the other acids can be produced by reacting the appropriate mono or dicarboxylic acid compound (free acid or acyl halide) with a suitable monohydroxy compound at a temperature of 60° to 200° C. or the dimethyl ester can be produced first and the appropriate diester produced by transesterification with a suitable monohydroxy compound at a temperature of 60° to 200° C.

The monohydroxy esters of polyphenyl carboxylic acids of my invention are useful as plasticizers of polyvinylchloride and other polymer formulations. Suitable monohydric alcohols useful for producing the ester include aromatic or aliphatic, straight or branched chain, substituted or unsubstituted compounds of from 1 to 24 carbon atoms. Examples are alcohols such as methyl alcohol, ethyl alcohol, propyl alcohol, butyl alcohol, isobutyl alcohol, 2-ethyl hexyl alcohol, amyl alcohol, hexyl alcohol, cyclohexyl alcohol, heptyl alcohol, dodecyl alcohol, octyl alcohol, isotridecyl alcohol, stearyl alcohol, oleyl alcohol, tetracosyl alcohol, as well as aromatic hydroxy compounds containing from 6 to 24 carbon atoms such as phenol, naphthol, cresol, para-stearylphenol, etc.

These esters can be produced under conventional reaction conditions by reacting from about 1 to 10 moles of monohydroxy compound per carboxyl equivalent of said acid compound to form a solution of ester and monohydroxy compound. If desired esterification catalysts or transesterification catalysts can be used, such as sulfuric acid, phosphoric acid, paratoluene sulfonic acid, benzene sulfonic acid, stannous octoate, boron trifluoride etherate, tetraalkyl titanates and zirconates of U.S. Pat. No. 3,056,818 etc.

The esters of monohydroxy compounds containing from 1 to 4 carbon atoms in each alkyl group can be used advantageously in ester interchange processes for producing high molecular weight polyesters while the esters containing from 1 to 24 carbon atoms in each ester moiety, preferably alkyl groups containing from about 4 to 13 carbon atoms, can be used as plasticizers for resinous polymers of vinyl chloride containing at least 50 mole percent vinyl chloride units. The resinous polymers of vinyl chloride include homopolymeric polyvinyl chloride, 95/5 vinyl chloride/vinyl acetate copolymers, etc. The plasticizers can be used in a concentration of from 5 to 300 parts by weight per each 100 parts by weight resinous polymer of vinyl chloride as the sole plasticizer or together with other plasticizers such as dioctyl phthalate, trioctyl phosphate, epoxidized glyceride oils, etc.

The polyphenyl dicarboxylic acids can be used to produce high molecular weight essentially linear condensation polymers, such as polyesters or polyamides. These can be made by condensing at least one of the novel diacyl compounds with an organic compound providing at least two reactive groups derived from either a polyhydric alcohol, a polyamine, a polyisocyanate or a polyisothiocyanate. These polyols, polyamines, polyisocyanates, or polythiocyanates can be saturated or unsaturated aromatic or aliphatic, straight or branched chain, substituted or unsubstituted.

In general, the highly polymeric essentially linear condensation polymers are resinous polymers consisting essentially of recurring units of an acyl compound wherein said acyl compound comprises a polyacyl radical of a methyl-substituted polyphenylcarboxylic acid of the structural formula

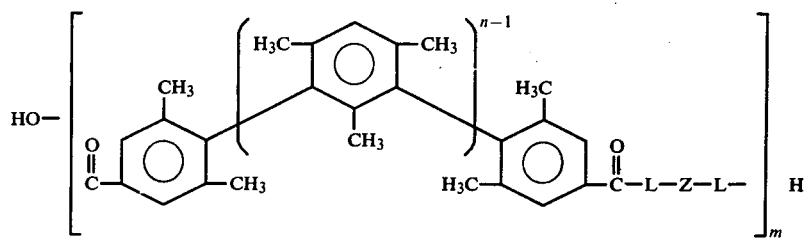

wherein n comprises a whole number from 1 to 3 inclusive; L is selected from the group consisting of

and —O— radicals, Z is selected from the group consisting of divalent aliphatic moieties and divalent aromatic moieties, m is a number of said recurring units wherein the said resinous polymer has an inherent viscosity of at least 0.20 dl/g in a 60/40 phenol-tetrachloroethane solvent at 30° C.

For purposes of this invention, the term "alkylene" is defined as including divalent groups having 2 to 20 carbon atoms in the alkylene chain. For purposes of this invention, the term "aromatic moiety" is defined as including divalent aromatic radicals characterized by at least one benzene ring, i.e., the six-carbon ring of benzene or the condensed six-carbon rings of the other aromatic radicals such as naphthylene, phenanthylene, anthrylene, etc. The term "aromatic moiety" is further defined as including radicals containing two benzene rings joined by a divalent group such as a methylene group, ether, sulfone, sulfide group, etc. Examples of these radicals are phenylene, biphenylene, diphenyleneether, diphenylenemethane, diphenylene sulfone, and diphenylenesulfide. One or more hydrogens of the aromatic nucleus can be replaced by non-reactive radical groups such as lower alkyls, halogens and nitro radicals.

The polyesters of this invention comprise a polyhydroxy component comprising one or more polyhydric alcohols (diols, triols, etc.) and a polycarboxylic acid component comprising one of the polyphenyl dicarboxylate components. The preferred polyesters of this invention are essentially linear and comprise units of alkylene glycols containing 2 to 10 carbon atoms and polyphenyl dicarboxylate moieties. The polyesters based on 2,2',6,6'-tetramethylbiphenyl-4,4'-dicarboxylate have an exceptionally high Tg. For example, homopolymeric polyethylene-2,2',6,6'-tetramethylbiphenyl-4,4'-dicarboxylate has a Tg of about 191° C. Molding temperature is about 240° C. Homopolymeric tetramethylene-2,2',6,6'-tetramethylene-4,4'-dicarboxylate has a Tg of 131° C. Homopolymeric polyethylene terephthalate has a Tg of about 70°–75° C. and a molding temperature of 260°–270° C. Homopolymeric polyethylene naphthalene 2,6-dicarboxylate has a Tg of 115°–125° C.

The glass transition and molding temperatures of polyesters of 2,2',6,6'-tetramethylbiphenyl-4,4'-dicarboxylic acid (M₂DA) and diols of chain lengths of up to ten carbon atoms as well as that of polyethylene terephthalate and other polyesters for comparison are given in the following table.

Table I

Thermal Properties of M₂DA and Other Polyesters

| Diacid | Diol | Tg° C. | Molding Temp. ° C. |
|---|---|---|---|
| 2,2',6,'-tetra-methylbiphenyl-4,4'- (M₂DA) | Ethylene Glycol | 191 | 240° |
| | 1,4-Butanediol | 131 | — |
| | 1,6-Hexanediol | 97 | — |
| | 1,10-Decanediol | 44 | — |
| Terephthalic | Ethylene Glycol | 70 | 260–270 |
| | 1,4-Butanediol | 22 | 240–250 |
| 2,6-Naphthalene | Ethylene Glycol | 115–125 | — |

Since wash and wear characteristics of textile produced from polyester fiber are a function of the Tg of the fiber, it is desirable to employ fibers having a Tg above 100° C. For example the Tg of the polyester of M₂DA and ethylene glycol is well over 100° C. The polyesters of this invention have a singular advantage over PET, i.e., 191° C. for the ethylene M₂DA polyester versus about 74° C., in wash and wear clothing. Truck tires have not been fabricated from polyester cords since the heat build up in the tires raises the temperature of the tire cord above 75° C. and the tire cord loses strength as it stretches. The lower molding temperature of the ethylene polyester of this invention than that of polyethylene terephthalate, 240° C. versus 260–270° C., reduces fabrication heat input with resulting economic utility.

Broadly speaking, the homopolymer polyesters are prepared by reacting a polyhydric alcohol with the dicarboxylic acid or lower alkyl (preferably methyl) ester of the dicarboxylic acid. An ester-forming derivative of the dicarboxylic acid may be used, i.e., an acid halide, a salt, its anhydride and/or an ester thereof, particularly an ester of the dicarboxylic acid with a lower aliphatic alcohol or with phenol. Correspondingly, ester-forming derivatives of the polyhydric alcohols may be employed, i.e., a derivative of the alcohol containing functional groups equivalent to the hydroxyl groups in their ability to react with carboxyl groups. Thus, an alcohol may be employed in the form of an epoxide, and/or ester of the alcohol with acetic acid or other lower aliphatic acid may be used.

In a convenient method for preparing the dihydric alcohol dicarboxylate polyester, the dimethyl ester of the dicarboxylic acid or acids is reacted with an excess of the polyhydric alcohol, 1.1 to 2.5 moles of polyol per mole of ester, preferably employing about 1.5 to 2.1 moles of polyol per mole of ester. A typical example is the reaction of ethylene glycol with dimethyl terephthalate. The reaction is usually carried out at atmospheric pressure but higher or lower pressure may be used if desired. A range is usually from 0.1 to ten atmospheres. Temperature is usually from 90° to 325° C. Following the ester interchange reaction, in which methanol is removed as a by-product, heating is continued at an increased temperature to bring about polycondensation. Small amounts of catalysts are usually added to facilitate the reaction, manganous acetate, calcium acetate, and sodium methoxide being typical ester interchange catalysts and antimony trioxide, dibutyltin maleate, and zinc acetate are suitable polycondensation catalysts. Litharge, sodium hydrogen hexabutoxytitanate and the tetra-alkyl titanates, such as tetra-isopropyl titanate, are examples of catalysts which may be used for both the ester interchange and the polycondensation steps. Normally, the polycondensation reaction is continued until a degree of polymerization is achieved corresponding to an inherent viscosity of approximately at least 0.3 dl/g in a 60/40 phenol-tetrachloroethane solvent at 30° C.

To achieve a higher degree of polymerization, the product of the polycondensation reaction is allowed to cool to room temperature, about 20° to 25° C., forming a solid material. The solid is ground to flake, following which the flake is heated below its melting point in a stream of inert gas to achieve solid phase condensation.

The polyhydric alcohols useful for producing the polyesters of this invention include alkylene glycols containing from about 2–12 carbon atoms, such as ethylene glycol, 1,2-propylene glycol, 1,3-propylene glycol, butylene glycol, hexamethylene glycol, dodecamethylene glycol, etc.; aromatic polyhydric alcohols such as hydroquinone, resorcinol, Bisphenol A, etc.; cycloaliphatic glycols such as 1,4-dimethylol cyclohexane, dimethylol cyclobutane, etc.; polyoxyalkylene glycols such as polyoxyethylene glycols, polyoxypropylene glycols, block copolymers of polyethylene and polypropylene glycol, polytetramethylene glycols, etc.; neopentyl glycol, polyhydric alcohols having three or more hydroxy groups, such as 1,1,1-trimethylol ethane, 1,1,1-trimethyol propane, pentaerythritol, sorbitol, etc.

The essentially linear polycarbonamides of this invention can be viewed as polyphenyl dicarboxamides having arylene and/or alkylene groups joining the amide groups of the polymer. One or more of the alkylene or arylene groups can be joined by one or more heteroatoms

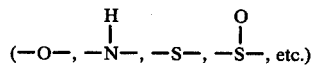

as is common in this art.

Suitable alkylene groups containing 2 to 24 carbon atoms include ethylene, trimethylene, hexamethylene, octamethylene, dodecamethylene,

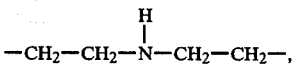

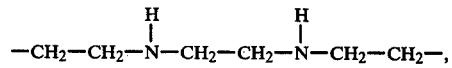

tetracosene, etc. Suitable arylene groups containing 6 to 24 carbon atoms include paraphenylene, orthophenylene, N,N-diphenyleneamine, oxydiphenylene, etc.

The high molecular weight polyamides can be prepared by well-known methods. These methods include reacting a dicarboxylic acid or its derivatives such as acid chlorides with alkylene and arylene diamines, diisocyanates, diisothiocyanates and their derivatives. For example, polyamides can be prepared from the free acid (2,2',6,6'-tetramethylbiphenyl-4,4'-dicarboxylic acid) and difunctional nitrogen-containing compounds such as diphenylmethane-4,4'-diisocyanate, diphenylether-4,4'-diisocyanate, 4,4'-diaminodiphenylmethane, paraphenylene diamine, etc.

In somewhat greater detail, the dicarboxylic acid can be reacted with an excess of the arylene diamine, diisocyanate, or diisothiocyanate (1.1 to 2.5 moles of reactant per mole of acid, preferably about 1.5 to 2.1 moles of reactant per mole of acid). The reaction can be carried out at atmospheric pressure but higher or lower pressure can be used if desired. The temperature is usually from about 90° to 325° C. Small amounts of catalyst can be added to facilitate the reaction. Normally, the reaction is continued until the desired degree of polymerization is achieved.

PREPARATORY EXAMPLE A

The starting materials, the polymethyl-substituted benzenes and their homologues, were prepared as is described in the following example.

The electrolysis cell consisted of a sealed glass tube two inches in diameter and 18 inches long, held vertically in a support. The tube was equipped with a take-off sidearm to return the electrolyte to the reservoir. The tube had a glass taper joint on the top of the tube to receive the glass input tube. The two electrode leads were inserted into the bottom of the tube using standard taper joints. The electrolyte input was supplied through the top of the tube. A one-half inch glass feed tube was extended to the bottom of reactor vessel through the glass stopper which sealed the taper joint. Two platinum screen electrodes, each of approximately 275 square centimeter in surface area, insulated from each other by a polyethylene screen, were connected to the electrode leads at the bottom of the reactor. A circulating pump supplied electrolyte from a reservoir, 1.5–3.0 liters, to the feed tube at 20 liters/minute.

The reservoir was charged with 1.5 liters electrolyte which was 0.1 molar tetraalkylamoniumtetrafluoroborate and 2.0 molar concentration of mesitylene in acetonitrile as the solvent. Specifically, 42 grams of tetrapropylammonium tetrafluoroborate and 360 grams of mesitylene were dissolved in acetonitrile to make 1.5 liters of final solution.

The above reaction mixture was subjected to electrolysis for seven and three-quarters hours. Current density was approximately 0.01 amperes/centimeter squared. The resulting mixture was then placed in a cooler overnight and held at −20° C. The next day about 37 grams of solids and heavy liquids were separated. The electrolysis was repeated with the addition of a fresh batch of 37 grams of mesitylene to the electrolyte. The procedure was repeated until a total of eight runs had been made using two batches of electrolyte, each of which was approximately three liters. Current densities were up to 0.055 amperes/centimeter squared. Total mesitylene used was 2,280 grams or 19 moles, which received 9.35 faradays of current, or approximately 0.5 faradays/mole. The batches were vacuum-stripped as made in a five-liter flask to remove the acetonitrile and some unreacted mesitylene. Pot temperature was 48°–50° C. at 3.0 mm Hg. The residue was extracted three times with 100 ml. portions of ethyl ether. The vestigial ether was removed by atmospheric distillation to a pot temperature of 114° C. The solids and heavy liquids recovered after each run were added together and the total quantity vacuum distilled. Pot temperature was 106° C., head temperature 63° C. at 3.0 mm Hg. to remove unreacted mesitylene. The bimestyl fraction was obtained from the residue with a pot temperature of 135°–187° C., head temperature of 118°–152° C. at 0.9 mm Hg. The termesityl fraction was obtained with a pot temperature of 202°–252° C., head temperature 149°–215° C. at 0.9 mm Hg.

The yields of the fractions obtained as well as the analyses are shown in Table II. The nuclear magnetic resonance (NMR) readings reported are in parts per million (ppm) in terms of the increment ($\delta$) from the standard tetramethylsilane (TMS). The readings are of the chemical shift of the hydrogen located in the positions (a) through (e). When n is 1 to 4 similar readings are obtained by NMR analysis for

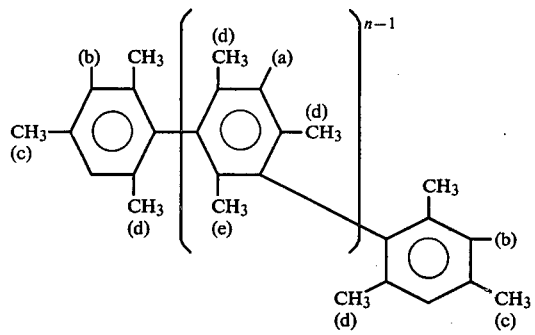

equivalent hydrogen positions for termesityls, quatermesityls, and quinquemesityls in the (a) and (e) positions. The yield of co-produced higher homologues, after separation by distillation, is shown as decreasing with increasing molecular weight. Current efficiency is defined as the ratio × 100 of actual weight to theoretical weight where theoretical weight is the equivalent weight times faradays.

TABLE II

| | Electrochemical Production of Bimesityl and Homologues Yields and NMR Analysis | | | | | | | | |
|---|---|---|---|---|---|---|---|---|---|
| | Yield Wgt. Grams | Current Efficiency % | M.P. °C. | B.P. °C./mmHg | $\delta$ Shift From The Standard - in ppm Hydrogen Position | | | | |
| | | | | | a | b | c | d | e |
| Bimesityl | 615 | 55 | 105–107 | 120–140/1.0 | n.a. | 6.82 | 2.32 | 1.88 | n.a. |
| Termesityl | 145 | 17 | 139–140 | 175–185/1.0 | 6.95 | 6.82 | 2.30 | 1.90 | 1.45 |
| Quatermesityl | >50 | | 223–224 | 235–255/1.2 | 6.96 | 6.80 | 2.30 | 1.90 | 1.48 |
| Quinquemesityl | >15 | 18 | 253–260 | >290/2.3 | 6.96 | 6.84 | 2.28 | 1.89 | 1.49 |
| Hexamesityl and Above | >50 | | N.D. | N.D. | — | — | — | — | — |
| Polymer | 13 | 2 | N.D. | N.D. | — | — | — | — | — |

Internal Standard - Tetramethyl Silane
Solvent - Deutero-Chloroform Chloroform (CDCl$_3$)
N.D. - Not Determined
n.a. - Not Applicable

EXAMPLE I

Fifteen grams cobaltous acetate was stirred in 200 ml. of acetic acid in a 500 ml three-necked round-bottom flask equipped with a thermometer, condenser, dropping funnel, electric heating mantle and magnetic stirrer. Fifteen ml. of 40 percent peracetic acid dissolved in acetic acid were added slowly to the flask from the dropping funnel. The color of the reactants changed from red (Co++) to green (Co+++) in an exothermic reaction. Five to ten minutes after the heat of reaction subsided, external heat was applied by the mantle to increase the temperature to 45° C. After ten grams bimesityl were added, the dropping funnel was replaced with a gas dispersion tube. Oxygen was introduced at 0.3 SCFH, measured at 25° C. and atmospheric pressure. When the reaction temperature reached approximately 95° C. (within range of 90°-115 as indicated in Table III), current to the mantle was adjusted to maintain such temperature for five hours. Thereafter oxygen introduction, stirring and external heating were stopped and the mixture allowed to cool to ambient temperature. The mixture was then filtered to obtain the precipitated solids, 2.7 grams, which were washed three times with 5 ml. of acetic acid. The filtrate was saved. The solids were then washed with concentrated hydrochloric acid to regenerate the free carboxylic acids from the 2.7 grams of precipitated solids. The regenerated acids were approximately 80% diacid and 20% monoacid.

The initial filtrate produced in the previous paragraph was poured into one liter of water, the precipitate filtered out, washed with more water, and then dissolved in 200 ml of ether. Extraction of the ether with 5% sodium bicarbonate (NaHCO$_3$) followed by acidification and filtration of the water extract yielded a fraction that was 85-90% the biphenyl diacid. A similar extraction with 5% potassium hydroxide (KOH) then gave a fraction that was 90-95% the biphenyl monoacid. The residue after ether evaporation was mainly unreacted bimesityl. The amounts of the various acids in these fractions were composited and the results tabulated to give the results shown in Table III. Table III lists pertinent data on four runs of selective bimesityl oxidation obtained by these methods.

TABLE III

Selective Oxidation of Bimesityl and Products Obtained

| Run | Reagents 10 Grams Bimesityl | | Temp ° C. | % Weight of Starting Materials | | | |
|---|---|---|---|---|---|---|---|
| | Co(OAc)$_2$-4H$_2$O | 40 % CH$_3$COOOH | | DA | MA | TA | Others |
| 1 | 10.1 | 10.0 | 90-104 | 29 | 45 | 1 | 4 |
| 2 | 10.0 | 9.9 | 100-105 | 25 | 48 | 1 | 3 |
| 3 | 10.0 | 10.1 | 112-114 | 12 | 46 | <0.5 | 3 |
| 4 | 15.0 | 15.1 | 99-102 | 39 | 35 | 1 | 3 |

DA —Diacid (2,2',6,6'-tetramethylbiphenyl-4,4,'-dicarboxylic acid)
MA —Monoacid (2,2',4,6,6'-Pentamethylbiphenyl-4'-carboxylic acid)
TA —May be tri-acids
Others —Probably aldehydes and/or alcohols Analysis of these extracted fractions by nuclear magnetic resonance (NMR) was used to identify the major components present. Esterification gas chromatography (EGC) then indicated the quantitative percent of the major component together with the number and concentration of intermediates and by-products. The mass spectra of the esters from EGC also confirmed the identification of the major component and gave good evidence of the structure of the intermediates and by-products.

The methyl esters were prepared using a 5 liter three-necked flask equipped with a thermometer, condenser and mechanical stirrer. A separatory funnel and a one-inch ten-tray fractionating column were also used.

The crude diacid fractions (511 gms.) were mixed with 2.75 liters of methanol and 700 grams of dry hydrochloric acid in the 5 liter three-necked flask and heated at reflux (70°-73° C.) for 48 hours. The reaction mixture was cooled to room temperature and the precipitated solids were removed by filtration with a Buchner funnel. The precipitate was washed twice with methanol and dried. The methanol-soluble esters were recoverable by evaporating the methanol washings. The methanol-washed esters, 349 grams, were dissolved in 2.8 liters of ethyl ether. The solution was extracted five times in the separatory funnel, once with 60 ml of a 5% solution of sodium carbonate in water, once with 70 ml. of a 5% solution of sodium hydroxide in water and three times each with 100 ml of water. The solution was dried overnight over anhydrous calcium sulfate. The calcium sulfate was filtered out and the ethyl ether stripped off using atmospheric distillation. The residue was then vaccum flashed to a pot temperature of 270° C. at 9-11 mm of Hg. The flashed esters were then fractionally distilled in a one-inch ten-tray fractionating still to separate the diacid esters and the monoacid esters. The diacid esters were then recrystallized from benzene and vacuum dried. The dimethyl-2,2',6,6'-tetramethylbiphenyl-4,4'-dicarboxylate melted at 128°-129° C.

The benzene-free diacid was recovered by heating the ester in KOH solution, acidifying with hydrochloric acid to excess hydrogen ion. The precipitated diacid was recovered by filtration. A water wash followed by drying under vacuum completed the purification procedure of the 2,2',6,6'-tetramethylbiphenyl-4,4'-dicarboxylic acid.

EXAMPLE II

The oxidation procedure in Example I was repeated using termesityl prepared by anodic coupling.

Ten grams cobaltous acetate were stirred in 200 ml. of acetic acid. 9.8 Grams of 40% peracetic acid in acetic acid were added. After the color of the reactants changed to green, external heat was applied. Ten grams termesityl were added, oxygen was introduced at 0.3 SCFH. When the reaction temperature reached approximately 106° C., the temperature was maintained for five hours. After the mixture was cooled, filtration yielded 0.2 grams of precipitated solids, which were not further worked up. An ether extraction of the initial filtrate which had been water washed was extracted with 5% sodium bicarbonate, acidified and filtered to yield a 2.1 gram fraction. This fraction analyzed by NMR was 30% monoacid (2,2',2'',4,4',6,6',6''-octamethyl-m-terphenyl-4''-carboxylic acid) and 70% diacid (2,2',2'',4'6,6',6''-heptamethyl-m-terphenyl-4,4''-dicarboxylic acid).

The crude acid fractions (4.8 grams) were esterified in a well-known gas chromatography esterification procedure. Twenty ml. methanol in twenty ml. pyridine containing the crude acid were heated to 100° C. for 15 minutes. Forty-five ml. trimethyl phosphate were added. Temperature was increased to 130° C. and rose to 175° C. through heat of reaction. After the mixture cooled to ambient temperature, chloroform extraction and distillation yielded fractions identified as the mono and diacid esters. A 0.9 gram fraction was 90% monoacid ester (methyl-2,2',2'',4,4',6,6',6''-octamethyl-m-terphenyl-4''-carboxylate). A 1.7 gram fraction was 81% diacid ester (dimethyl-2,2',2'',4',6,6',6''-heptamethyl-m-terphenyl-4,4''-dicarboxylate). Analysis was by gas chromatography.

EXAMPLE III

The oxidation procedure in Example I was repeated using quatermesityl prepared by anodic coupling.

Fifteen grams cobaltous acetate were stirred in 200 ml. of acetic acid. Fifteen grams of 40% peracetic acid in acetic acid were added. Ten grams of quatermesityl were oxidized at a reaction temperature of 90°–93° C. for seven hours. Filtration yielded 0.2 grams of precipitated solids. Carbonate extraction of the ether extract yielded a 1.2 gram fraction. A 5% potassium hydroxide extraction yielded a 5.0 gram fraction. The five gram fraction was esterified in a gas chromatography esterification procedure as in Example II. The 5.0 gram esterified fraction was 45.7% monoacid ester (methyl-2,2',2'',2''',4,4',4'',6,6',-6'',6'''-undecamethyl-m-quaterphenyl-4'''-carboxylate), 44.5% diacid ester (dimethyl-2,2',2'',2''',4',4'',6,6',6'',6'''-decamethyl-m-quaterphenyl-4,4'''-dicarboxylate) and 2.3% triacid ester which was not further characterized. Analysis was by mass spectrograph.

Table IV lists the NMR and mass spectra analyses of the methylsubstituted polyphenylcarboxylic acids of Examples I, II and III.

EXAMPLE VI

This example illustrates the preparation of biphenyl pentacarboxylic acid by severe oxidation of bimesityl by the method of U.S. Pat. No. 2,833,816 which is incorporated by reference. Three preparations were made.

The oxidation reactor was a suitable pressure reactor having a corrosion resistant inner surface, such as glass, ceramic, or corrosion resistant metal as titanium or alloy, e.g., a titanium pressure vessel three feet long and three inches in diameter equipped with means of agitation such as gas flow through the end of the reactor or a mechanical agitating device, and with means for heating the reactor contents to 225° C. or cooling rapidly to ambient temperatures the contents thereof such as a coil or jacket, reflux condenser for refluxing the solvent during the reaction, a gas inlet tube for nitrogen, a vent gas outlet for oxygen and nitrogen, a thermometer and manometer for measuring temperature and pressure.

The reaction vessel was charged with the following solvent mix for batch oxidation:

1250 ml of acetic acid containing 50 ml of water
3.96 gm cobalt acetate tetrahydrate
7.85 gm manganese acetate tetrahydrate
0.16 gm sodium bromide
0.42 ml. tetrabromoethane.

A feedstock of bimesityl, e.g. 230 gms. was introduced with the solvent mix into the reaction vessel through the top of the reactor. Said mixture was heated to 188° C. under a nitrogen gauge pressure of 250 psi (17.6 kg/sq cm) and then air was introduced into the reaction mixture through the bottom of the said reactor as an oxygen source and for agitation. The condenser refluxed the solvent through the oxidation.

When the oxygen content of the exhaust gas from the reactor reached 18%, the reaction was terminated by introducing nitrogen and discontinuing the heating. The reactor and its contents were then cooled to ambient

TABLE IV

NMR and Mass Spectra Analyses Methyl-Substituted Polyphenylcarboxylic Acids

NMR Analysis- δ Shift From The Standard - In ppm

| Example | Name | Hydrogen Position | | | | | Solvent |
|---|---|---|---|---|---|---|---|
| | | a | b | c | d | e | |
| I | 2,2',4,6,6'Pentamethyl-biphenyl-4'-carboxylic acid | n.a. | 6.90 | 2.31 | 1.95 | n.a. | CDCl$_3$ |
| | | n.a. | 7.83 | — | 1.83 | n.a. | |
| I | 2,2',6,6'-Tetramethyl-biphenyl-4,4'-dicarboxylic acid | n.a. | 7.68 | — | 1.88 | n.a. | NaOD in D$_2$O |
| II | 2,2',2'',4,4',6,6',6''-Octamethyl-m-terphenyl-4''-carboxylic acid | 7.07 | 6.92 | 2.30 | 1.87 | 1.42 | CDCl$_3$ |
| | | — | 7.86 | — | 1.98 | — | |
| II | 2,2',2'',4,6,6',6''-Heptamethyl-m-terphenyl-4,4''-dicarboxylic acid | 7.10 | 7.76 | — | 1.88 | 1.40 | CD$_3$OD |
| | | | | | 1.98 | | |
| III | 2,2',2'',2'''',4,4',4'',6,6',6'',6'''-Undecamethyl-m-quaterphenyl-4'''-carboxylic acid | 6.90 | 7.06 | 2.30 | 1.89 | 1.48 | CDCl$_3$ |
| | | 7.84 | — | — | 1.94 | — | |
| | | — | — | — | 2.00 | — | |

Note:
Internal Standard-Tetramethyl Silane
Solvent - Deutero-Chloroform (CDCl$_3$)
- Sodium Deuteroxide (NaOD) in Deuterium Oxide (D$_2$O)
- per Deutero-Methanol (CD$_3$OD)

Mass Spectra Analysis

| Example | Name | Molecular Wgt. | % of Total |
|---|---|---|---|
| III | 2,2',2'',2''',4'',4'',6,6',6'',6'''-Decamethyl-m-quaterphenyl-4,4'''-dicarboxylic acid (analyzed as the ester) | | |
| | Monoester of Quatermesityl Mono-acid | 518 | 45.7 |
| | Diester of Quatermesityl Di-acid | 562 | 44.5 |
| | Triester of Quatermesityl Tri-acid | 606 | 2.3 |

Note:
Low-voltage intensities expressed as % of total ionization temperature. The desired biphenyl polybasic acids were obtained in the form of a slurry in the reaction mixture. The entire reaction mixture was decanted from the reaction vessel and filtered to remove the poly-acid product. The acetic acid and by-product water were evaporated from the filtrate in a porcelain evaporating dish on a steam bath to obtain the solids remaining in the filtrate. Table V indicates the reaction conditions and yields obtained.

TABLE V

Batch Oxidation of Bimesityl To Biphenyl Pentacarboxylic Acid

| Run | (1) | (2) | (3) |
|---|---|---|---|
| Feed Wgt., gms | 230 | 225 | 100 |
| Moles of Feed | 0.97 | 0.94 | 0.44 |
| Conditions | | | |
| Pressure, psig | 250 | 250 | 250 |
| Initial Temperature, °C. | 193 | 193 | 193 |
| Maximum Temperature, °C. | 215 | 214 | 210 |
| Average Temperature, °C. | 213 | 213 | 204 |
| Run Time, Minutes | 78 | 53[3] | 30 |
| Wgt. % Metals (On Solvent) | 0.3 | 0.3 | 0.1 |
| Solvent/Feed, Wgt. | 6 | 6 | 8 |
| Atom Ratio - Co:Mn:Br. | 1:2:3 | 1:2:3 | 1:2:3 |
| Moles % $O_2$ Absorbed | 85 | 85 | 118 |
| Moles $CO_2$ Produced | 1.5 | 1.5 | 1.1 |
| Yields | | | |
| Wgt % Cake[1] | 64 | 65 | 45 |
| Wgt % Filtrate Solids[2] | 134 | 149 | 141 |
| Analysis | | | |
| Cake Acid Number (Theoretical 814) | 700 | 726 | Not Determined |

[1]Theory is 414/238 = 174 Wgt %
[2]Contained acetic acid
[3]Air rate was ⅓ faster in Run (2) than Run (1).

The 2-methylbiphenyl-2,4,4',6,6'-pentacarboxylic acid was isolated from the reaction mixture by esterification and fractionation and analyzed using nuclear magnetic resonance (NMR). Among the other products present and isolated was the hexamethyl ester of the hexacarboxylic acid.

TABLE VI

NMR Analysis - Biphenyl Pentacarboxylic Acid

| | | δ Shift from the Standard Hydrogen Position | | |
|---|---|---|---|---|
| Example | Name | b | d | Solvent |
| IV | 2-Methylbiphenyl 2',4,4',6,6' penta-carboxylic Acid | 8.02 8.51 8.70 | 1.92 — — | $CDCl_3$ |

Note:
Internal Standard - Tetramethyl Silane
Solvent - Deutero-Chloroform ($CDCl_3$)

EXAMPLE V

This example illustrates the production of high molecular weight polyamides and conversion into polyamide films suitable for high-temperature electrical insulation, typically having high dielectric constants.

One and one-half grams 2,2',6,6'-tetramethylbiphenyl-4,4'-dicarboxylic acid was dissolved in 5.8 grams of N-methyl-2-pyrrolidone in a small round-bottomed three-necked flask equipped with a thermometer, electric heating mmantle and magnetic stirrer. The solution was heated to 150°-170° C. with stirring. Over a period of 45 minutes, 1.25 grams of diphenylmethane-4,4'-diisocyanate was added while maintaining the temperature at 150°-170° C. with stirring. Carbon dioxide was evolved. The temperature of 170° C. was maintained for an additional hour after which an additional 0.25 grams of diphenyl methane 4,4' diisocyanate were added. Heating and stirring were continued for another 30 minutes at 170° C. The solution was then diluted with 3.0 grams of N-methylpyrrolidone to reduce the viscosity to Z5-Z6 (Gardener-Holdt) at 20% solids. A second dilution with 3.0 grams of N-methylpyrrolidone was then made to reduce solids to 15%. A clear solution with viscosity of 40 Stokes resulted.

The inherent viscosity of the polyamide was determined using a Cannon-Fensky viscosimeter. The inherent viscosity was measured at 25° C. at a concentration of 0.5% by weight of the polymer in dimethyl acetamide.

A film was then cast from a 15% weight solution upon glass plate and cured with heat. The Massachusetts Institute of Technology (MIT) film folding endurance test was used to measure film toughness.

EXAMPLE VI

Example V was repeated using 1.5 grams 2,2',6,6'-tetramethylbiphenyl-4,4'-dicarboxylic acid and 1.75 grams diphenylether 4,4'-diisocyanate in place of the diphenylmethane diisocyanate (the same mole ratio of reactants). Solvent was added to adjust the resultant polymer solution to 15% weight solids with a viscosity greater than Z6 (Gardner-Holdt) and equal to 148 Stokes. Inherent viscosity was determined at 0.5% weight and cast film toughness determined.

EXAMPLE VII

This example illustrates the production of a polyamide from 2,2',-6,6'-tetramethylbiphenyl-4,4'-diacyl chloride and a diamine. The diacid chloride derivative was prepared by refluxing overnight 2.0 gms of the diacid in 20 ml. of thionyl chloride with one drop of N,N-dimethylformamide as catalyst. Excess thionyl chloride was evaporated. The resulting crystalline residue was dried in a moderate vacuum at 50° C. for two days. The melting point was 197°-200° C.

The polyamide was prepared by reacting 2.2 gms of the diacid chloride derivative with 1.30 gms of methylene bisaniline in 15 gm of N,N-dimethyl acetamide (DMAC) as the solvent, at ambient temperature and pressure. The solvent mix was heated to 45°-50° C. for 45 minutes and then cooled to ambient temperature over a period of two hours. A clear viscous solution, viscosity 80 Stokes and 16% weight solids (calculated), resulted. DMAC was added to thin the polymer solution. Water was then added to precipitate the polymer which was separated by filtration. The crumbly granules of precipitated polymer were water-washed and dried overnight in a vacuum oven. The inherent viscosity at 0.5% weight concentration was determined. Cast film toughness was measured.

Product characterizations as to the films by the processes of Examples V to VII are summarized in Table VII.

TABLE VII

| | Polyamides From 2,2',6,6' Tetramethyl-4,4'-Dicarboxylic Acid | | |
|---|---|---|---|
| Example | Inherent Viscosity[1] | Solution Viscosity[2] | Film Folding Endurance[3] |
| V | 0.90 | 40 | 6500–10,000 (1.2 Mils) |
| VI | 1.08 | 150 | 300 (1.3 Mils) |
| VII | 0.86 | — | 15–50,000 (0.9 Mils) |

[1]0.5% in DMAC (N,N-dimethyl acetamide)
[2]15% solids in NMP (N-methyl-2-pyrrolidone)
[3]MIT Folding Endurance (Double Folds)

EXAMPLE VIII

This example illustrates the production of a high molecular weight homopolymeric polyethylene 2,2',6,6'-tetramethylbiphenyl-4,4'-dicarboxylate by ester interchange of the dimethyl ester with ethylene glycol in melt followed by solid state polymerization.

Five grams of dimethyl 2,2',6,6'-tetramethylbiphenyl-4,4'-dicarboxylate, 2.1 grams of ethylene glycol and 0.1 grams of dibutyl tin maleate were heated at 180°–185° C. in a test tube equipped with a nitrogen bubbler and a side-arm. During the heating, nitrogen was slowly bubbled through the mixture. After the mixture was heated for two hours, the nitrogen flow was discontinued. A partial vacuum was pulled on the mixture over a period of 10 to 15 minutes, using a vacuum pump attached to the side-arm, and when the temperature rose to 260° C. a full vacuum (0.2 mm Hg) was applied and held for two hours. Inherent viscosity of the product was 0.21 deciliters per gram (dl/g), measured at a concentration of 0.4 grams per deciliter in a 60:40 by weight mixture of phenol and symmetrical tetrachloroethane.

The above product was ground to #10 mesh and heated in a test tube at 200°–210° C. and 0.05 mm Hg vacuum for 32 hours. After 16 hours, the white homopolymeric ethylene 2,2',6,6'-tetramethylbiphenyl-4,4'-dicarboxylate had an inherent viscosity of 0.59 dl/g. After the second 16 hours, the inherent viscosity was 0.84 dl/g.

EXAMPLE IX

This example illustrates melt polymerization to a relatively high I.V. One hundred twenty grams dimethyl 2,2',6,6'-tetramethylbiphenyl-4,4'-dicarboxylate, 45.6 grams of ethylene glycol, 0.1 grams of dibutyl tin maleate, 0.05 grams of calcium acetate and 0.5 ml. of antimony trisbutoxide were heated to 200° C. for two hours in a round bottom flask equipped with a mechanical stirrer and two side-arms. Nitrogen was bubbled slowly through the mixture during the period of heating with stirring. After two hours a partial vacuum was pulled on the mixture for 10 to 15 minutes, using a vacuum pump attached to the side-arm. When the temperature rose to 260° C., a full vacuum (0.1–2.2 mm Hg) was applied with continued stirring and kept for 8.0 hours. Inherent viscosity of the light brown homopolymer was 0.87 dl/g measured as described earlier. Strong fibers could be pulled from the melt.

Polymerization data with several diols are in Table VIII.

Table VIII

| Diol | Diol Weight -Grams | M₂DMe Weight -Grams | Polymerization | Reaction Time Hrs/°C./mmHg | Catalyst Amount | Melt I.V. (dl/g) | Polymer I.V. (dl/g) | Tg °C. |
|---|---|---|---|---|---|---|---|---|
| Ethylene Glycol | | | Solid State | 16/200–210°/0.1 | None (Control) | 0.18 | — | — |
| Ethylene Glycol | 2.1 | 5.0 | Melt | 2/260/0.2 | Sb/0.1g | | 0.27 | 184 |
| Ethylene Glycol | | | Solid State | 16/200–210°/0.1 | Sb* | 0.30 | 0.64 | 191 |
| Ethylene Glycol | | | Solid State | 16/200–210/0.1 | Sn* | 0.21 | 0.59 | |
| Ethylene Glycol | | | Solid State | 32/200–210/0.1 | Sn* | 0.21 | 0.84 | |
| 1,4-Butanediol | 2.7 | 4.5 | Melt | 2/260/0.2 | Ti/0.05 ml | | 0.37 | 131 |
| 1,6-Hexanediol | 3.6 | 4.5 | Melt | 2/260/0.2 | Ti/0.05 ml | | 0.31 | 97 |
| 1,10-Decanediol | 3.8 | 4.1 | Melt | 2/260/0.2 | Sb/0.05 g, Sn/0.05 g | | 0.95 | 44 |

Sb - Antimony trisbutoxide
Sn - Dibutyl Tin Maleate
Ti - Tetra-n-butyl titanate
M₂DMe - Dimethyltetramethylbiphenyldicarboxylate
*Additional catalyst not utilized

EXAMPLE X

This example illustrates compression molding of a polyester film of this invention. Homopolymeric polyethylene 2,2',6,6'-tetramethylbiphenyl-4,4'-dicarboxylate (PEM₂) having an I.V. of 0.87 dl/g was dried at 120° C. and 635 mm (30 inches) Hg overnight and placed between aluminum sheets and spacers to obtain the desired thickness. The polyester was placed in a press at 240° C. and held under pressure for five minutes. The sample was then removed from the press and allowed to cool without pressure. A fiberglass blanket was used to cover the sample in order to slow the cooling rate. Using this procedure, a 0.87 dl/g polyester powder was molded to give a film with a 0.77 dl/g inherent viscosity. The inherent viscosity loss was approximately the same as would be observed for poly(ethylene terephthalate). For compression molding of thicker parts up to 125 mils, a ten minute heating time was employed with a picture frame mold instead of aluminum sheets.

Physical properties of the film and shaped molded parts made according to the above procedure are given in the following Table IX.

Table IX

| Properties of PEM₂ Film and Molded Parts | |
|---|---|
| Density, g/cm³ | 1.14 |
| Glass Transition Temperature, ° C. DTA | 191 |
| Rheovibron | 227 |
| Heat Deflection Temperature ° C., 264 psi | 172 |
| Ultimate Tensile Strength, psi | 7658 |
| Elongation at Break, % | 4.1 |
| Flexural Modulus, psi | 282,000 |
| Young's Modulus dyne/cm² | 1 × 10¹⁰ |
| Tensile Impact Strength, psi | 41 |
| Limiting Oxygen Index, % O₂ | 27–27.5 |

What is claimed is:

1. A resinous polymer of a methyl-substituted polyphenylcarboxylic acid compound wherein the said polymer has the structural formula

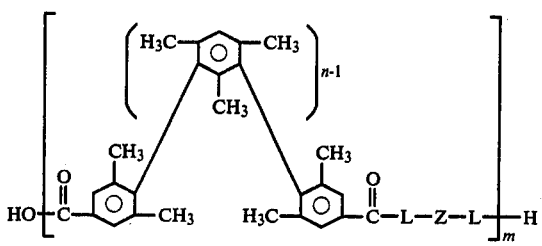

wherein n comprises a whole number from 1 to 3 inclusive, L is —O—, Z is selected from the group consisting of divalent aliphatic moieties and divalent aromatic moieties, m is a number of recurring units wherein the said resinous polymer has an inherent viscosity of at least 0.20 dl/g in a 60/40 phenol-tetrachloroethane solvent at 30° C.

2. The polymer of claim 1 wherein the said divalent aliphatic moiety comprises an alkylene group having 2 to 20 carbon atoms in the alkylene chain.

3. The polymer of claim 1 wherein said divalent aromatic moieties are selected from the group consisting of phenylene, biphenylene, diphenylene ether, diphenylenemethane, diphenylenesulfone, diphenylenesulfide, naphthylene, phenanthrylene and anthrylene moieties.

4. The polymer of claim 3 wherein said aromatic moieties comprise substituted moieties, said substitutions selected from the group of radicals consisting of lower alkyls, halogens, and nitro radicals.

5. The polymer of claim 1 wherein the said acid comprises 2,2',6,6'-tetramethylbiphenyl-4,4'-dicarboxylic acid.

6. The polymer of claim 5 wherein Z comprises ethylene and L is oxygen.

7. The polymer of claim 5 wherein Z comprises butylene.

8. The resinous polymer of claim 1 wherein the said polymer comprises a polyester of a methyl-substituted polyphenylcarboxylic acid compound and a polyhydric alcohol compound.

* * * * *

UNITED STATES PATENT OFFICE
CERTIFICATE OF CORRECTION

Patent No. 4,154,922    Dated May 15, 1979

Inventor(s) John A. Donohue

It is certified that error appears in the above-identified patent and that said Letters Patent are hereby corrected as shown below:

| Patent Column | Line | |
|---|---|---|
| 5 | 47 | "-6,6',6",6'"'6"'should be --6,6',6",6"',6""-- |
| 6 | 22 | "isopropanol," should be --isopropanol),-- |
| 9 (Table I) | 8 | "2,2',6'-tetra-" should be --2,2'6,6'-tetra- -- |
| 12 | 8 | "bimestyl" should be --bimesityl-- |
| 12 (Table II) 3rd line from end | 55 | "Deutero-Chloroform Chloroform" should be --Deutero-Chloroform-- |
| 12 | 50-55 | Bracket in Table II should be opposite >50, >15 and >50 |
| 15 (Table IV under "Name", Example III) | 55 | "2,2',2",2"",4,4',4",6,6',6",6"'-" should be --2,2',2",2"',4,4',4",6,6',6",6"'- -- |
| 15 (Table IV, under "Name" EXAMPLE III, bottom section) | 65 | "2,2',2",2"',4",4",6,6',6",6"'-Decamethyl-" should be --2,2',2",2"',4',4",6,6',6",6"'-Decamethyl- -- |

UNITED STATES PATENT OFFICE
CERTIFICATE OF CORRECTION

Patent No. 4,154,922          Dated May 15, 1979

Inventor(s) John A. Donohue

It is certified that error appears in the above-identified patent and that said Letters Patent are hereby corrected as shown below:

| Patent Column | Line | |
|---|---|---|
| 16 | 1 | "EXAMPLE VI" should be --EXAMPLE IV-- |
| 17 | 33 | "2-methylbiphenyl-2,4,4',6,6'-pentacarboxylic" should be --2-methylbiphenyl-2',4,4',6,6'-pentacarboxylic |
| 17 | 61 | "mmantle" should be --mantle-- |

Signed and Sealed this

Thirtieth Day of September 1980

[SEAL]

Attest:

SIDNEY A. DIAMOND

Attesting Officer          Commissioner of Patents and Trademarks